United States Patent
Kwon et al.

(10) Patent No.: US 11,601,353 B2
(45) Date of Patent: Mar. 7, 2023

(54) DEVICE IDENTIFICATION APPARATUS AND METHOD BASED ON NETWORK BEHAVIOR

(71) Applicant: ELECTRONICS AND TELECOMMUNICATIONS RESEARCH INSTITUTE, Daejeon (KR)

(72) Inventors: Hyeok-Chan Kwon, Daejeon (KR); Byung-Ho Chung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 17/507,730

(22) Filed: Oct. 21, 2021

(65) Prior Publication Data

US 2022/0150145 A1    May 12, 2022

(30) Foreign Application Priority Data

Nov. 12, 2020    (KR) ........................ 10-2020-0151267

(51) Int. Cl.
| | |
|---|---|
| G06F 15/16 | (2006.01) |
| H04L 43/065 | (2022.01) |
| H04L 9/40 | (2022.01) |
| H04L 41/16 | (2022.01) |
| H04L 67/12 | (2022.01) |

(52) U.S. Cl.
CPC ............ *H04L 43/065* (2013.01); *H04L 41/16* (2013.01); *H04L 63/20* (2013.01); *H04L 67/12* (2013.01)

(58) Field of Classification Search
CPC ........ H04L 43/065; H04L 41/16; H04L 63/20
See application file for complete search history.

(56) References Cited

U.S. PATENT DOCUMENTS

| | | | |
|---|---|---|---|
| 8,150,318 B2 | 4/2012 | Moon et al. | |
| 9,729,416 B1* | 8/2017 | Khanal | ................. H04L 41/145 |
| 2010/0080202 A1* | 4/2010 | Hanson | ............... H04W 12/084 370/338 |
| 2013/0091085 A1 | 4/2013 | Sohn et al. | |
| 2013/0139263 A1* | 5/2013 | Beyah | ................. H04L 63/1408 726/23 |
| 2019/0215339 A1 | 7/2019 | Chen | |
| 2020/0236112 A1* | 7/2020 | Pularikkal | ............. H04L 41/145 |
| 2021/0191640 A1* | 6/2021 | Ponnala | ................ G06F 3/0641 |

FOREIGN PATENT DOCUMENTS

| | | |
|---|---|---|
| KR | 10-2001813 B1 | 7/2019 |
| KR | 10-2020-0098838 A | 8/2020 |

* cited by examiner

*Primary Examiner* — Padma Mundur
(74) *Attorney, Agent, or Firm* — LRK Patent Law Firm (57) ABSTRACT

Disclosed herein are a device identification apparatus and method based on network behavior. The device identification apparatus includes one or more processors, and execution memory for storing at least one program that is executed by the one or more processors, wherein the at least one program is configured to collect packet data of a device connected to a network through port mirroring and extract behavior features from the packet data, analyze the behavior features and then generate unique information based on a previously created detection model, and extract an identification number corresponding to the unique information from a database and then identify the device.

18 Claims, 9 Drawing Sheets

DEVICE IDENTIFICATION APPARATUS AND METHOD BASED ON NETWORK BEHAVIOR

CROSS REFERENCE TO RELATED APPLICATION

This application claims the benefit of Korean Patent Application No. 10-2020-0151267, filed Nov. 12, 2020, which is hereby incorporated by reference in its entirety into this application.

BACKGROUND OF THE INVENTION

1. Technical Field

The present invention relates generally to security management technology for devices, and more particularly to technology for automatically identifying a device based on network behavior.

2. Description of Related Art

A large number of devices may be installed on a network, and various types of services may be provided by identifying the devices on the network. For example, currently, in large-scale medical institutions, such as tertiary referral hospitals and general hospitals, from thousands of medical devices to tens of thousands of medical devices may be installed and operated. Among such medical devices, many medical devices are connected to a network, and a considerable number of medical devices provide medical services while the locations thereof change.

However, no function of automatically identifying medical devices connected to the network and automatically detecting the locations of the medical devices (physical locations and connection locations in a network structure) is currently available. Accordingly, in general, there are many cases where the locations of medical devices must be manually input, or are not comprehensively managed when the medical devices are moved. Then, from the standpoint of hospitals, for a considerable number of medical devices, in particular, for medical devices that are serviced while moving (i.e., at various locations), it is currently impossible to check in real time which medical device is being serviced, and at which location.

When medical devices can be automatically identified and the locations thereof on the network can be detected, various types of services for medical device security management, such as management of medical devices, control of access by the medical devices to the network, management of a network access control list for each piece of network equipment, and establishment of security policies, can be provided.

Currently, among medical devices, when a certain medical device is compliant with a standardized protocol, such as Digital Imaging Communication in Medicine (DICOM) or Health Level (HL7), which is a dedicated medical protocol for network communication, it is possible to identify the certain medical device by checking the content of protocol packets. However, currently, there are multiple medical devices that are not compliant with standardized medical network protocols. In this case, manufacturers often establish and use arbitrary communication protocols, whereby medical devices cannot be identified through packet checking. Further, even for medical devices that are compliant with a standardized protocol such as HL7 or DICOM, it is difficult to detect the medical devices when inaccurate information is inserted into packets. Furthermore, it is difficult to install software, such as a separate agent, in medical devices used in hospitals due to the characteristic of medical devices whereby availability thereof is considered to be the highest priority, thus making it impossible in practice to install some software in medical devices for device identification.

Meanwhile, Korean Patent No. 10-2001813, entitled "Apparatus and Method for Detecting Abnormal Behavior of Nonstandard Protocol Payload Using Deep Neural Network Algorithm" discloses an apparatus and method for detecting abnormalities in devices. Here, this technology includes a data packet collection module for collecting data packets compliant with nonstandard protocols in real time in an industry control system environment, parses the data packets collected by the data packet collection module in real time, generates a payload mask pattern, and thereafter analyzes the data packets collected in real time through deep-learning based on a Deep-Neural Network (DNN) algorithm, thus detecting abnormalities in the corresponding device.

SUMMARY OF THE INVENTION

Accordingly, the present invention has been made keeping in mind the above problems occurring in the prior art, and an object of the present invention is to automatically identify a device when the corresponding device is operated in the state in which the device is connected to a network.

Another object of the present invention is to provide efficient device management by identifying network access information for a device, the physical location of the device, etc.

A further object of the present invention is to provide additional security functions, such as access control for a device and establishment of security policies for the corresponding network.

In accordance with an aspect of the present invention to accomplish the above objects, there is provided a device identification apparatus based on network behavior, including one or more processors, and execution memory for storing at least one program that is executed by the one or more processors, wherein the at least one program is configured to collect packet data of a device connected to a network through port mirroring and extract behavior features from the packet data, analyze the behavior features and then generate unique information based on a previously created detection model, and extract an identification number corresponding to the unique information from a database and then identify the device.

The at least one program may be configured to collect the packet data of the device from a port of a router into which the device plugs, through the port mirroring.

The at least one program may be configured to extract behavior features from the packet data collected in a process whereby access by the device to the network is initialized.

The at least one program may be configured to extract behavior features from packet data collected depending on a re-operation of the device after access by the device to the network has been initialized.

The at least one program may be configured to extract the behavior features from an average data volume of the packet data, a protocol, a port, an operation cycle, and a communication pattern.

The at least one program may be configured to generate the unique information through time-series packet analysis using a predefined deep-learning technique.

The at least one program may be configured to, when a result of determining a similarity between unique information stored in the database and the unique information generated from the behavior features is equal to or greater than a preset threshold, extract the identification number corresponding to the unique information stored in the database.

The at least one program may be configured to identify the device corresponding to the identification number from the database and ascertain a pre-registered physical location of the device.

The at least one program may be configured to, when the behavior features are changed, extract an identification number corresponding to the database from unique information of the changed behavior features and check a change in a physical location of the device.

The at least one program may be configured to establish a security policy and a security level for the device from the identification number and provide a security management service corresponding to the security policy and the security level to the device.

In accordance with another aspect of the present invention to accomplish the above objects, there is provided a device identification method based on network behavior, the device identification method being performed by a device identification apparatus based on network behavior, the device identification method including collecting packet data of a device connected to a network through port mirroring and extract behavior features from the packet data, analyzing the behavior features and then generating unique information based on a previously created detection model, and extracting an identification number corresponding to the unique information from a database and then identifying the device.

Extracting the behavior features may be configured to collect the packet data of the device from a port of a router into which the device plugs, through the port mirroring.

Extracting the behavior features may be configured to extract behavior features from the packet data collected in a process whereby access by the device to the network is initialized.

Extracting the behavior features may be configured to extract behavior features from packet data collected depending on a re-operation of the device after access by the device to the network has been initialized.

Extracting the behavior features may be configured to extract the behavior features from an average data volume of the packet data, a protocol, a port, an operation cycle, and a communication pattern.

Generating the unique information may be configured to generate the unique information through time-series packet analysis using a predefined deep-learning technique.

Identifying the device may be configured to, when a result of determining a similarity between unique information stored in the database and the unique information generated from the behavior features is equal to or greater than a preset threshold, extract the identification number corresponding to the unique information stored in the database.

Identifying the device may be configured to identify the device corresponding to the identification number from the database and ascertain a pre-registered physical location of the device.

Identifying the device may be configured to, when the behavior features are changed, extract an identification number corresponding to the database from unique information of the changed behavior features and check a change in a physical location of the device.

Identifying the device may be configured to establish a security policy and a security level for the device from the identification number and provide a security management service corresponding to the security policy and the security level to the device.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

In the present specification, it should be understood that terms such as "include" or "have" are merely intended to indicate that features, numbers, steps, operations, components, parts, or combinations thereof are present, and are not intended to exclude the possibility that one or more other features, numbers, steps, operations, components, parts, or combinations thereof will be present or added.

Hereinafter, preferred embodiments of the present invention will be described in detail with reference to the attached drawings.

Figure 1:
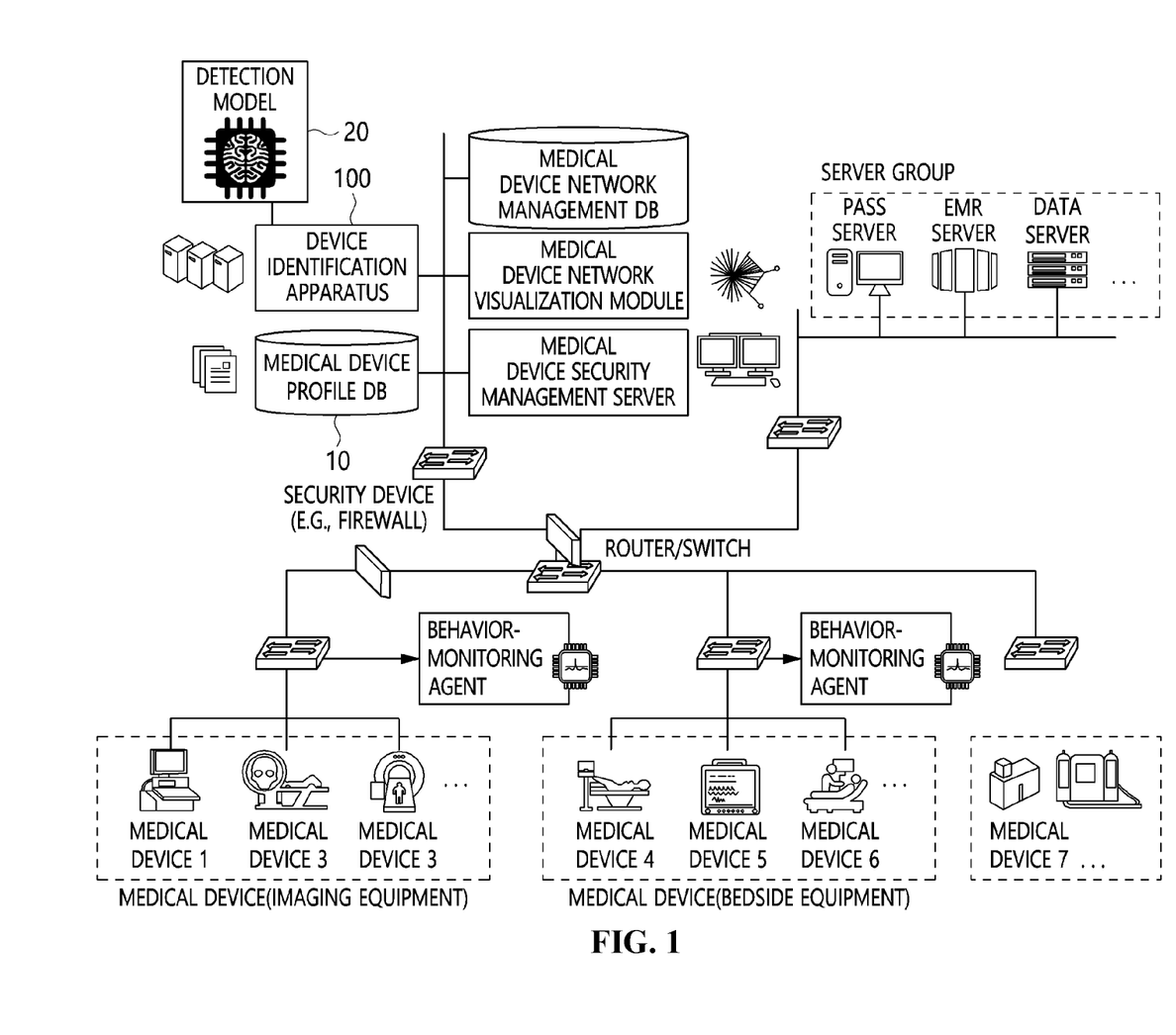
FIG. 1 is a diagram illustrating a network system according to an embodiment of the present invention.

FIG. 1 is a diagram illustrating a network system according to an embodiment of the present invention.

Referring to FIG. 1, it can be seen that the network system according to the embodiment of the present invention is a network system to which medical devices are connected.

The network system according to the embodiment of the present invention may include a medical device profile database (DB) 10, a device identification apparatus 100 based on network behavior (hereinafter also referred to as a "network-behavior-based device identification apparatus 100"), a medical device network management DB, a medical device network visualization module, a medical device security management server, a behavior-monitoring agent, a server group, and multiple medical devices.

The behavior-monitoring agent may be a software or hardware module, which is connected to a router (or a switch), into which each medical device plugs, and which provides functions of collecting packet data that is transmitted or received by the corresponding medical device and transferring the packet data to the network-behavior-based device identification apparatus 100.

Here, the network-behavior-based device identification apparatus 100 may mirror the packet data by performing port mirroring on the router through the behavior-monitoring agent.

The network-behavior-based device identification apparatus 100 may learn behavior features from network behavior expressed by each medical device, and may generate unique information about the medical device from the behavior features.

Here, the unique information may correspond to identifiers, information, or the like required in order to identify various devices, such as phenotype fingerprints.

Here, the network-behavior-based device identification apparatus 100 may generate and learn a phenotype fingerprint, and may then create a detection model.

Here, the network-behavior-based device identification apparatus 100 may analyze behavior features from the network behavior expressed by the medical device, may compare the analyzed behavior features with the previous phenotype fingerprint generated above, and may then identify the medical device.

The medical device profile DB 10 may store basic profile information of each medical device (e.g., an identification number, category, type, model, manufacturer, manufacture date, purchase date, Medicare Administrative Contractor (MAC) information, etc.) and the phenotype fingerprint information generated through learning of the network behavior expressed by the medical device.

The medical device security management server, which is a server that manages the security of medical devices in hospitals, may provide a function of establishing and managing security policies for each medical device.

Here, when the corresponding medical device is identified, the medical device security management server may provide a function of transferring and indicating security settings to security equipment, such as a router or firewall to which the medical device is connected.

The medical device network visualization module may provide a visualization view that allows a manager to visually manage the automatically identified medical device and the security thereof based on the information about the automatically identified medical device (i.e., the location of the medical device, profiles, etc.).

The medical device network management DB may store the identification number of the medical device and variable information of the medical device (e.g., the IP address, current physical location, etc.).

Here, the medical device network management DB may also store security-related information such as security policies and rule sets that are managed by the medical device security management server, together with the above-described information.

Here, the medical device network management DB may manage information in real time.

The server group may include various servers connected to the network, such as a Professional Association for SQL Server (PASS), an Electronic Medical Record (EMR) server, and a data server.

The medical devices may include various medical appliances such as imaging equipment and bedside equipment.

Figure 2:
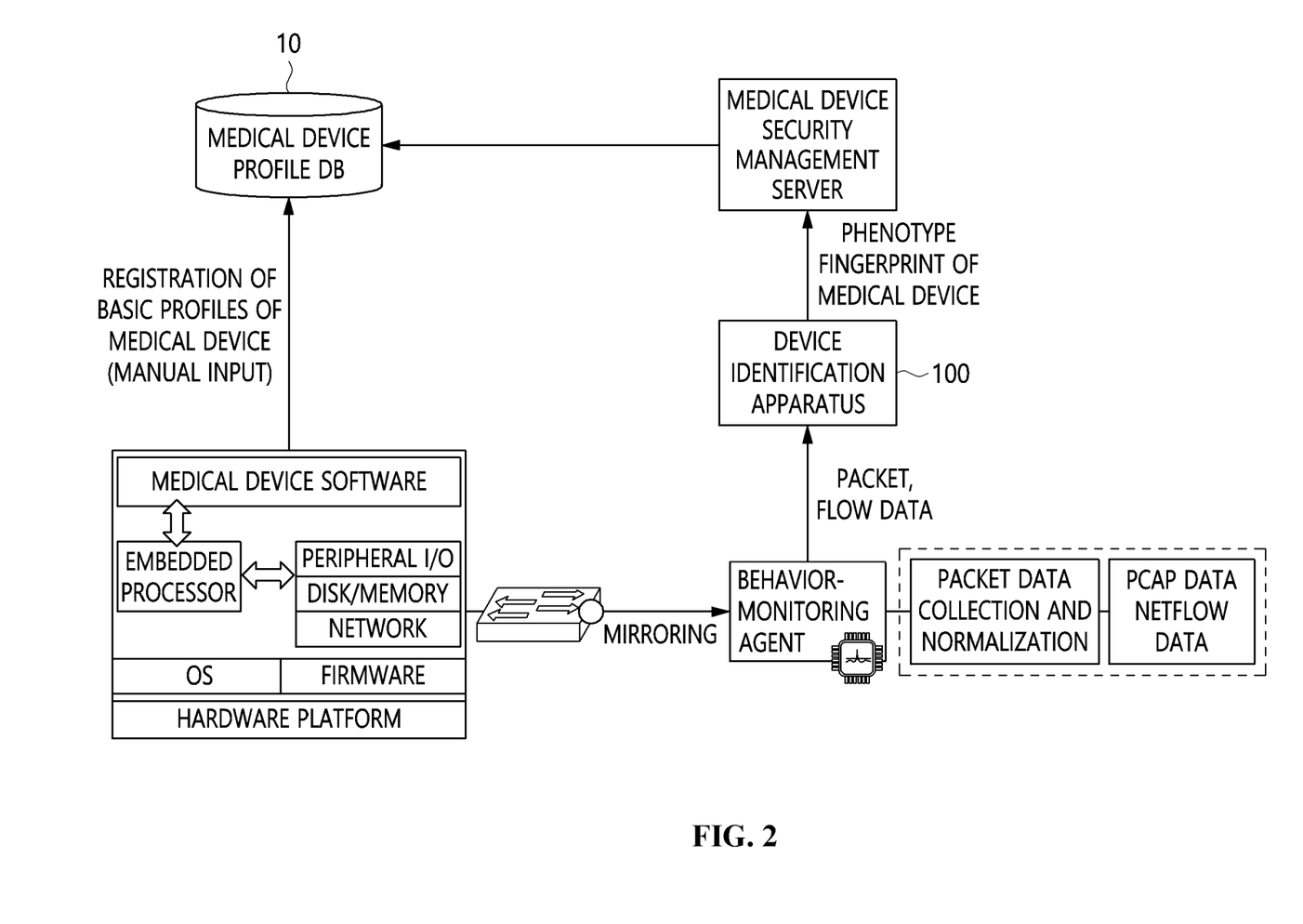
FIG. 2 is a diagram illustrating a process for extracting and analyzing behavior features by a device identification apparatus based on network behavior according to an embodiment of the present invention.
Figure 3:
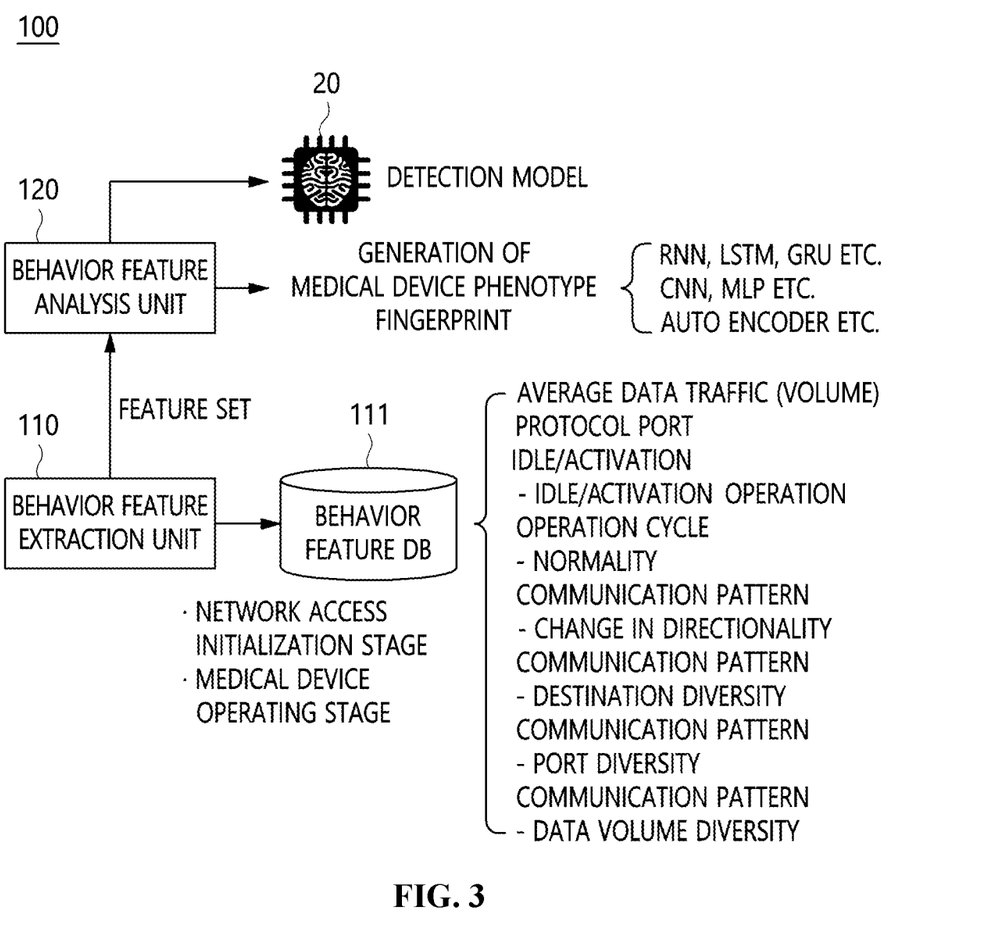
FIG. 3 is a block diagram illustrating a device identification apparatus based on network behavior for performing extraction and analysis of behavior features according to an embodiment of the present invention.

FIG. 2 is a diagram illustrating a process for extracting and analyzing behavior features by a device identification apparatus based on network behavior (i.e., a network-behavior-based device identification apparatus) according to an embodiment of the present invention. FIG. 3 is a block diagram illustrating a device identification apparatus based on network behavior for performing extraction and analysis of behavior features according to an embodiment of the present invention.

Referring to FIG. 2, the network-behavior-based device identification apparatus 100 according to the embodiment of the present invention may generate a phenotype fingerprint of a medical device when the medical device is initially installed and operated in a hospital.

In this case, because the network-behavior-based device identification apparatus 100 requires network behavior data for learning/analysis, the medical device is operated for a certain time, and then packet data is collected for a preset time, after which behavior features may be extracted from the packet data and used to generate the phenotype fingerprint.

The medical device is connected to the network (by plugging into a router/switch) and is then operated.

The behavior-monitoring agent may collect packet data that is transmitted or received by the medical device connected to the network through port mirroring on the router (or switch) to which the medical device is connected.

Here, the behavior-monitoring agent may transmit the collected packet data and flow data to the network-behavior-based device identification apparatus 100.

Because software such as an agent cannot be installed in the medical device due to the characteristic of the medical device whereby availability thereof is considered to be the highest priority, the behavior-monitoring agent may collect packet data by mirroring ports on the router to which the medical device is connected, without being installed in the medical device.

The network-behavior-based device identification apparatus 100 may analyze the collected data and then extract behavior features from the collected data.

Referring to FIG. 3, the network-behavior-based device identification apparatus 100 includes a behavior feature extraction unit 110, a behavior feature DB 111, and a behavior feature analysis unit 120.

The behavior feature extraction unit 110 may collect packet data through port mirroring by a behavior-monitoring agent, and may extract behavior features from the packet data.

Here, the behavior feature extraction unit 110 may store the extracted behavior features in the behavior feature DB 111.

The behavior feature DB 111 may store and manage behavior features corresponding to information about average data traffic (volume), a protocol, a port, an operation cycle, and a communication pattern so as to analyze the network behavior of the medical device.

The average data volume may correspond to the average amount of data that is transmitted in one operation.

The information about the protocol and the port may correspond to information about the protocol used by the medical device and information about a network access port.

The operation cycle may include information about an idle/activation (active) ratio and regularity.

The idle/activation ratio may correspond to operating characteristics, for example, characteristics indicating whether data is transmitted in a periodic pattern, whether the medical device is mainly in an idle state and intermittently transmits data, and how long the medical device is maintained in an active state once it is operated.

Regularity may correspond to information indicating whether the distribution of the operation of the medical device appears to be periodic or aperiodic.

The communication pattern may correspond to information about a change in directionality, destination diversity, port diversity, and data volume diversity.

The change in directionality may correspond to the change in transmission and reception directionality for communication.

The destination diversity may correspond to the number of destinations to which a packet is to be transmitted, the distribution of communication target destinations, etc.

The port diversity may correspond to information about how many ports are used and which types of ports are used.

The data volume diversity may correspond to the normality or the like of distribution of the amount of data that is transmitted whenever data transmission is performed.

Also, the network-behavior-based device identification apparatus 100 may collect behavior features, store the collected behavior features in the behavior feature DB 111, and utilize the behavior features for learning, depending on two situations.

The network-behavior-based device identification apparatus 100 may extract behavior features of the medical device on the network in the process for initializing network access at the beginning of operation, such as the case where the medical device plugs into the network in a network access initialization stage for the medical device or where the corresponding medical device is powered on.

In this case, in the network access initialization stage for the medical device, invalid behavior features, among the above-defined behavior features, may be included.

The behavior feature analysis unit 120 may create a detection model 20 by learning the behavior features, and may generate a phenotype fingerprint, which is unique information of the medical device. The phenotype fingerprint may be an Artificial Intelligence (AI) model obtained through AI learning.

Here, in a medical device operation stage after network access is initialized, the behavior feature analysis unit 120 may collect packet data during the process for operating the medical device, and may learn behavior features extracted from the packet data.

Here, the behavior feature analysis unit 120 may learn the behavior features using time-series packet analysis through a Recurrent Neural Network (RNN), Long Short-Term Memory (LSTM), a Gated Recurrent Unit (GRU) model, or the like.

Here, as the occasion demands, the behavior feature analysis unit 120 may learn the behavior features while being merged with a Convolutional Neural Network (CNN), a Multilayer Perceptron (MLP), a statistical model, a machine-learning model, or the like.

In this case, the behavior feature analysis unit 120 may utilize a scheme for dividing or rearranging a recursive neural network through an auto-encoder.

Here, the behavior feature analysis unit 120 may transmit the generated phenotype fingerprint of the medical device to the medical device security management server.

The medical device security management server may store the phenotype fingerprint of the corresponding medical device in the medical device profile DB 10.

Figure 4:
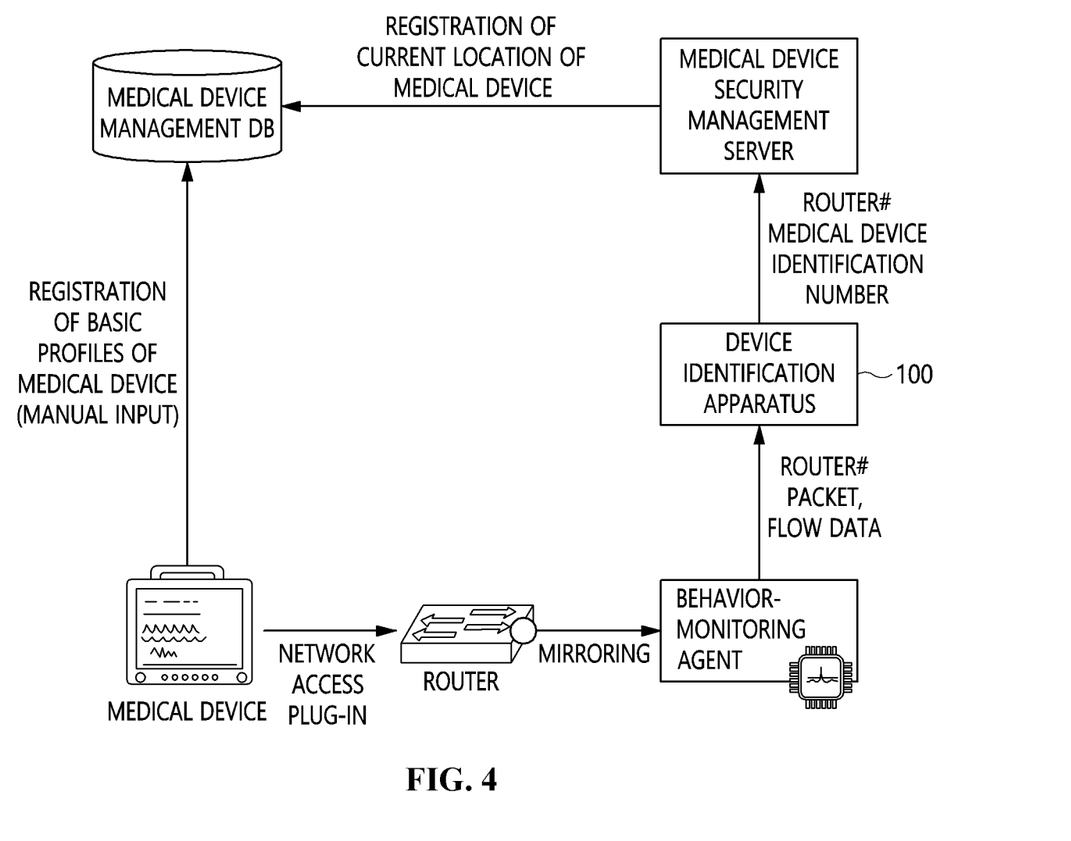
FIG. 4 is a diagram illustrating a device identification process performed by a device identification apparatus based on network behavior according to an embodiment of the present invention.
Figure 5:
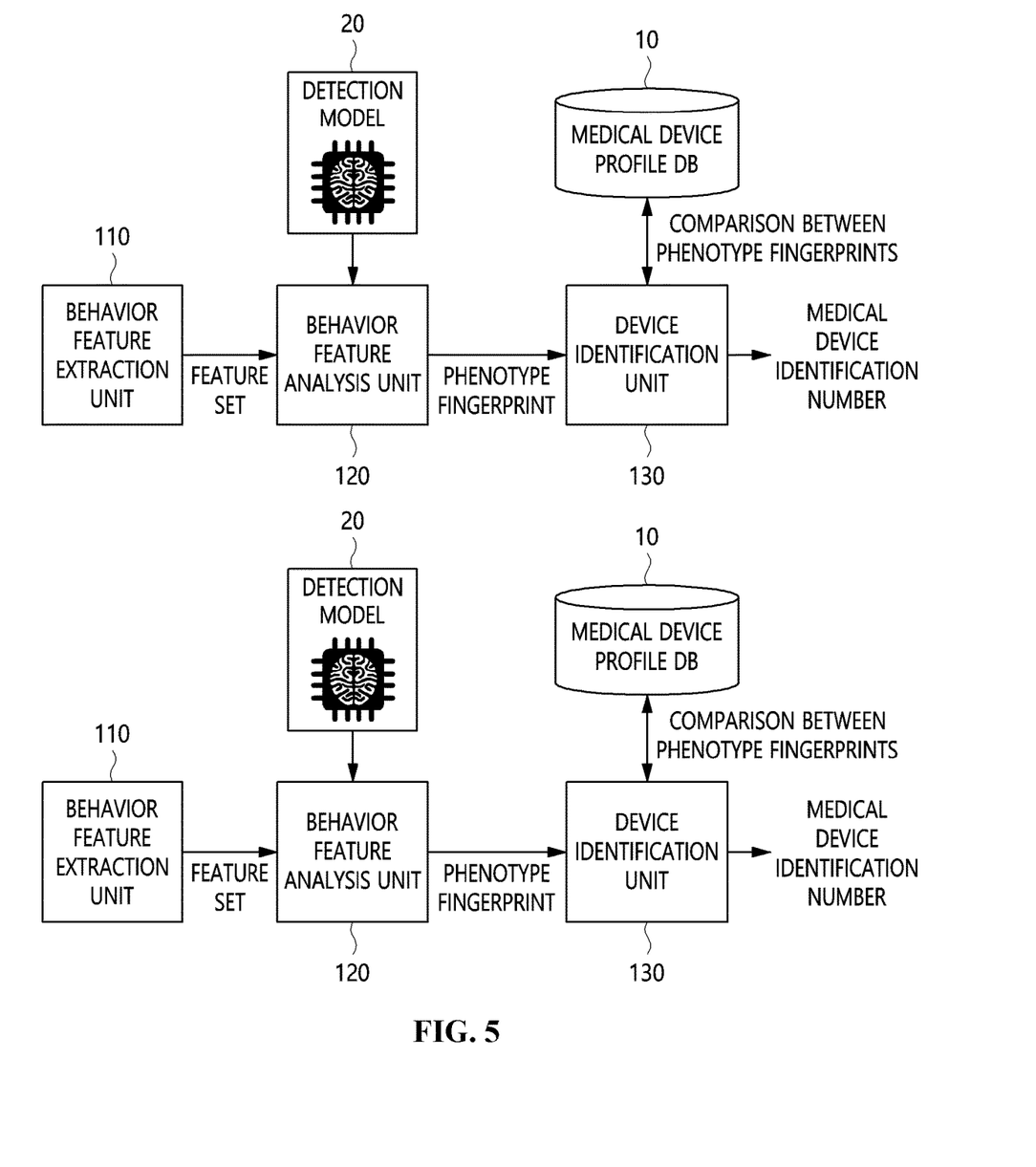
FIG. 5 is a block diagram illustrating a device identification apparatus based on network behavior, which performs device identification, according to an embodiment of the present invention.

FIG. 4 is a diagram illustrating a device identification process performed by a device identification apparatus based on network behavior according to an embodiment of the present invention. FIG. 5 is a block diagram illustrating a device identification apparatus based on network behavior, which performs device identification, according to an embodiment of the present invention.

Referring to FIG. 4, after the network-behavior-based device identification apparatus 100 has generated a phenotype fingerprint and stored the phenotype fingerprint in advance in the medical device profile DB 10, the identification process may be performed when the medical device is connected to the network.

First, a medical device may be connected to and operated on the network (by plugging into a router/switch).

Here, the behavior-monitoring agent may collect packet data and flow data that is transmitted or received by the connected medical device through port mirroring on the router (or switch) to which the medical device is connected, and may transmit the collected packet data and flow data to the network-behavior-based device identification apparatus 100.

The network-behavior-based device identification apparatus 100 may analyze the behavior features of the medical device based on a previously created detection model, and may generate a phenotype fingerprint, as described above with reference to FIGS. 2 and 3.

Here, the network-behavior-based device identification apparatus 100 may compare the phenotype fingerprint with phenotype fingerprints previously stored in the medical device profile DB, and may then extract the identification number of the medical device.

In this case, when the similarity between the corresponding phenotype fingerprint and one of the stored phenotype fingerprints is equal to or greater than a preset threshold value required to determine similarity between the phenotype fingerprints, the network-behavior-based device identification apparatus 100 may determine that the medical device is identified.

Referring to FIG. 5, the network-behavior-based device identification apparatus 100 includes a behavior feature extraction unit 110, a behavior feature analysis unit 120, and a device identification unit 130.

The behavior feature extraction unit 110 may collect packet data of a medical device connected to the network through port mirroring, and may extract behavior features from the packet data.

Here, the behavior feature extraction unit 110 may collect the packet data of the medical device from the port of a router into which the medical device plugs, through port mirroring.

Here, the behavior feature extraction unit 110 may extract behavior features from the packet data collected in the process whereby access by the medical device to the network is initialized.

Here, the behavior feature extraction unit 110 may extract behavior features from packet data collected depending on the re-operation of the medical device after access by the medical device to the network has been initialized.

The behavior feature extraction unit 110 may extract behavior features from the average data volume of the packet data, a protocol, a port, an operation cycle, and a communication pattern.

The behavior feature analysis unit 120 may analyze the behavior features based on the previously created detection model, and may then generate a phenotype fingerprint, which is unique information.

Here, the behavior feature analysis unit 120 may generate the phenotype fingerprint, which is the unique information, through time-series packet analysis using a predefined deep-learning technique.

The device identification unit 130 may extract an identification number corresponding to the unique information from the medical device profile DB 10, and may then identify the medical device.

In detail, when the result of determining the similarity between the phenotype fingerprint stored in the medical device profile DB 10 and the phenotype fingerprint generated from the behavior features is equal to or greater than a preset threshold value, the device identification unit 130 may extract an identification number corresponding to the phenotype fingerprint stored in the medical device profile DB 10.

Here, the device identification unit 130 may transmit the extracted medical device identification number and the identification number of the router/switch, to which the medical device is connected, to the medical device security management server.

The medical device security management server may check the physical location at which the router is installed based on the router identification number, may ascertain the physical location of the detected medical device, may notify the network-behavior-based device identification apparatus 100 of information about the physical location and network access information (e.g., the IP address, the router to which the medical device is connected, etc.), and may store the physical location information and the network access information in a medical device management DB.

The device identification unit 130 may identify the medical device corresponding to the identification number from the medical device profile DB 10, and may check the pre-registered physical location of the medical device from the medical device security management server.

Here, when the behavior features are changed, the device identification unit 130 may extract an identification number corresponding to the medical device profile DB 10 from a phenotype fingerprint corresponding to the changed behavior features, and may verify the change in the physical location of the medical device.

Here, the device identification unit 130 may establish a security policy and a security level for the medical device based on the identification number, and may provide security management service corresponding to the security policy and the security level to the medical device.

Figure 6:
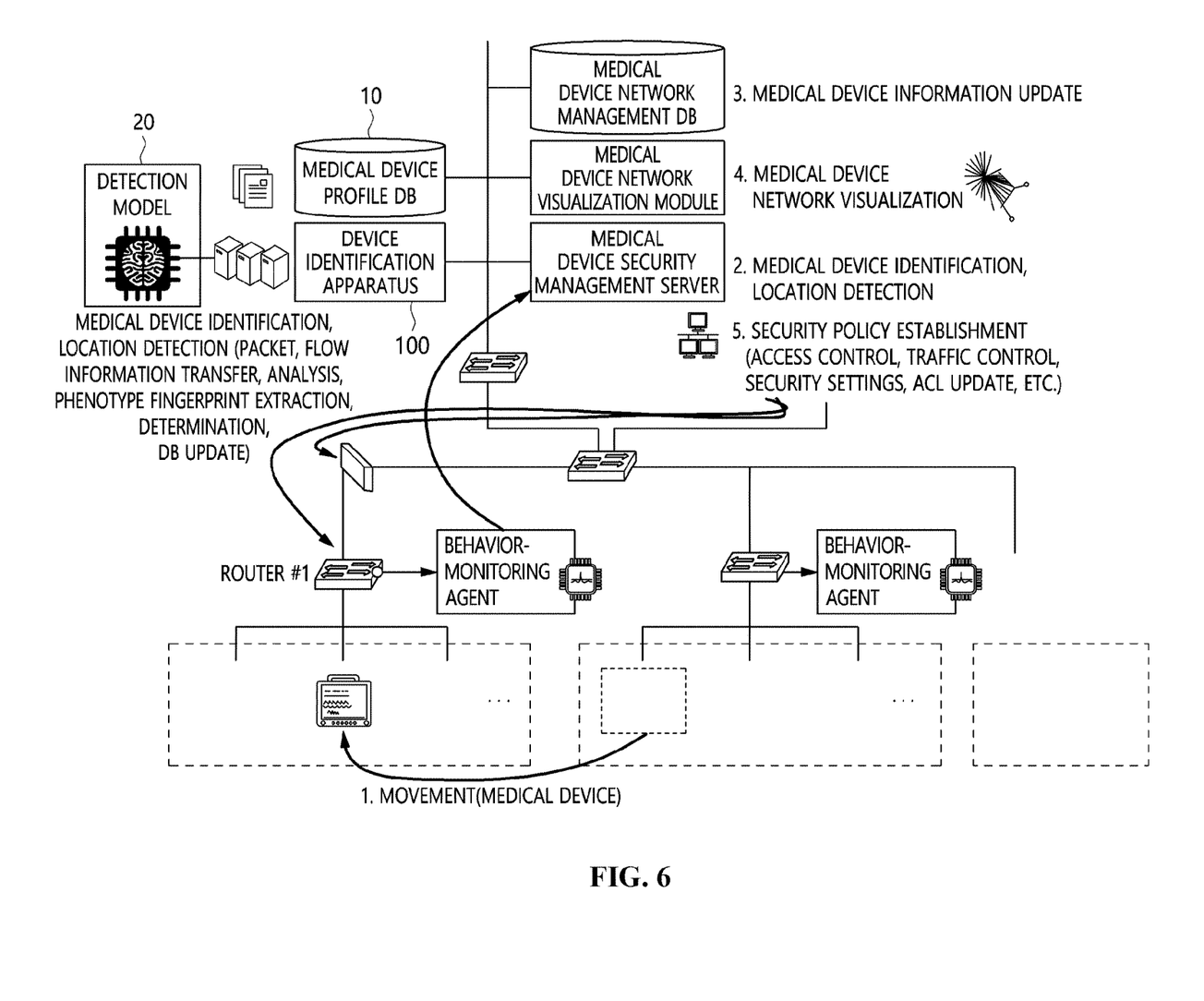
FIG. 6 is a diagram illustrating a security service based on medical device identification information according to an embodiment of the present invention.

FIG. 6 is a diagram illustrating a security service based on medical device identification information according to an embodiment of the present invention.

Referring to FIG. 6, the security service based on medical device identification information according to the embodiment of the present invention may be provided through movement of a medical device (e.g., plugging into another network), automatic identification of the medical device, and real-time information update of the medical device (e.g., the IP address of the medical device, the physical location of the medical device, the status of the medical device, etc.).

A medical device network visualization service may be provided to a manager by adding access information and status information of the corresponding medical device to the visualization dashboard of a hospital network through a medical device network visualization module.

A medical device security service may establish a security policy depending on the update of medical device access information.

Here, when software (SW) capable of executing the corresponding function is installed in a router, the medical device security service may establish a security policy depending on the category, security level, and policy of the corresponding medical device in the router/switch to which the medical device is connected.

For example, the medical device security service may control access by the medical device (permission/denial), may establish the security level (in the case of a medical device requiring high security, activation of an abnormality detection module through additional packet analysis, or the like), and may update an Access Control List (ACL).

Here, when there is additional security equipment in a network domain that the medical device accesses, the medical device security service may establish the category of the medical device, the security level of the medical device, and the security policy corresponding to the security level in the security equipment of the network domain that the medical device accesses.

For example, the security equipment of the network domain may include a firewall, an Intrusion Detection System (IDS), etc.

For example, the security policy may include access control for the medical device (permission/denial), establishment of a security level, update of an Access Control List (ACL), etc.

For example, the establishment of the security level may include, for example, activation of an abnormality detection module, etc. through packet analysis in the case of a medical device requiring high security.

Figure 7:
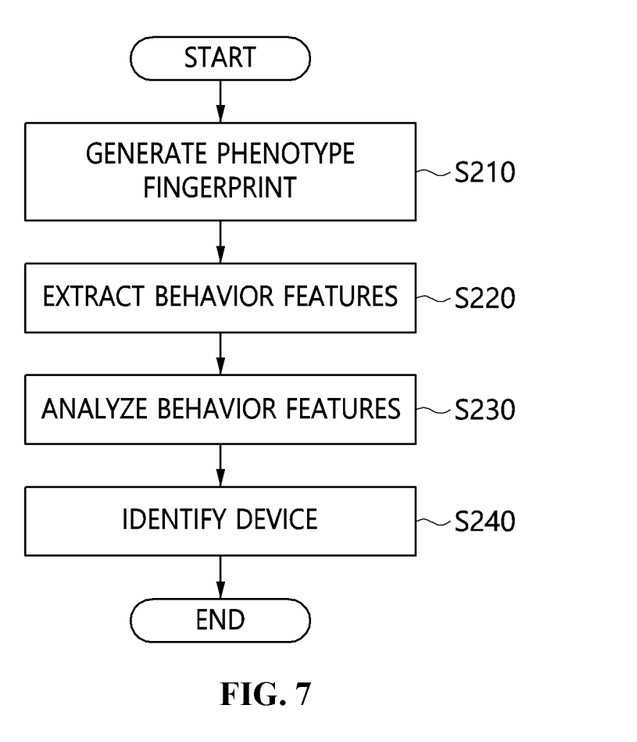
FIG. 7 is an operation flowchart illustrating a device identification method based on network behavior according to an embodiment of the present invention.

Referring to FIG. 7, the device identification method based on network behavior according to the embodiment of the present invention may generate a phenotype fingerprint at step S210.

That is, at step S210, packets may be collected from a medical device, behavior features may be extracted from the packets, a detection model may be created, and a phenotype fingerprint, which is unique information of the medical device, may be generated based on the detection model.

Figure 8:
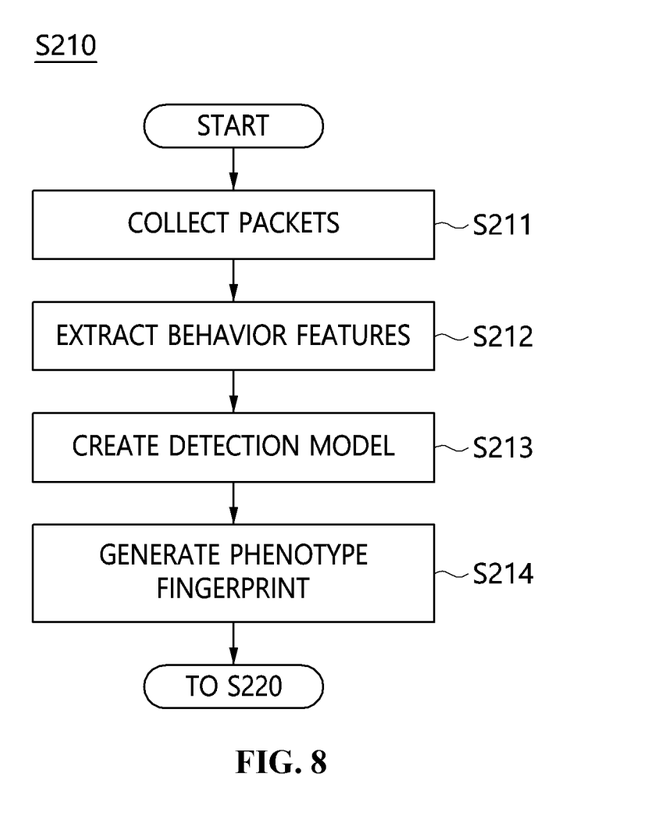
FIG. 8 is an operation flowchart illustrating in detail an example of the phenotype fingerprint generation step illustrated in FIG. 7.

Referring to FIG. 8, at step S210, packet data may be collected through port mirroring by a behavior monitoring agent at step S211.

Also, in the procedure at step S210, behavior features may be extracted from the packet data at step S212.

Here, at step S212, the extracted behavior features may be stored in the behavior feature DB 111.

Here, at step S212, behavior features corresponding to information about average data traffic (volume), a protocol, a port, an operation cycle, and a communication pattern may be stored and managed so as to analyze the network behavior of the medical device.

The average data volume may correspond to the average amount of data that is transmitted in one operation.

The information about the protocol and the port may correspond to information about the protocol used by the medical device and information about a network access port.

The operation cycle may include information about an idle/activation (active) ratio and regularity.

The idle/activation ratio may correspond to operating characteristics, for example, characteristics indicating whether data is transmitted in a periodic pattern, whether the medical device is mainly in an idle state and intermittently transmits data, and how long the medical device is maintained in an active state once it is operated.

Regularity may correspond to information indicating whether the distribution of the operation of the medical device appears to be periodic or aperiodic.

The communication pattern may correspond to information about a change in directionality, destination diversity, port diversity, and data volume diversity.

The change in directionality may correspond to the change in transmission and reception directionality for communication.

The destination diversity may correspond to the number of destinations to which a packet is to be transmitted, the distribution of communication target destinations, etc.

The port diversity may correspond to information about how many ports are used and which types of ports are used.

The data volume diversity may correspond to the normality or the like of distribution of the amount of data that is transmitted whenever data transmission is performed.

Here, at step S212, the behavior features may be collected and stored in the behavior feature DB 111, and may be utilized for learning, depending on two situations.

Here, at step S212, behavior features of the medical device on the network may be extracted in the process for initializing network access at the beginning of operation, such as the case where the medical device plugs into the network in a network access initialization stage for the medical device or where the corresponding medical device is powered on.

In this case, in the network access initialization stage for the medical device, invalid behavior features, among the above-defined behavior features, may be contained.

Further, in the procedure at step S210, a detection model 20 may be created by learning the behavior features at step S213.

Here, at step S213, in the medical device operating stage after initialization of network access, packet data during a process for operating the medical device may be collected, and behavior features extracted from the packet data may be learned.

Here, at step S213, the behavior features may be learned using time-series packet analysis through a RNN, LSTM, a GRU model, or the like.

At step S213, as the occasion demands, the behavior features may be learned through merging with a CNN, an MLP, a statistical model, a machine-learning model, or the like.

At step S213, a scheme for dividing or rearranging a recursive neural network through an auto-encoder may be utilized.

Here, at step S213, the detection model 20 may be created from the results of learning the behavior features.

Furthermore, in the procedure at step S210, a phenotype fingerprint, which is the unique information of the medical device, may be generated at step S214. The phenotype fingerprint may correspond to an Artificial Intelligence (AI) model through AI learning.

Here, at step S214, the generated phenotype fingerprint of the medical device may be transmitted to the medical device security management server.

Here, at step S214, a medical device security management server may store the phenotype fingerprint of the corresponding medical device in the medical device profile DB 10.

Next, the device identification method based on network behavior according to the embodiment of the present invention may extract behavior features at step S220.

That is, at step S220, packet data of a medical device connected to the network may be collected through port mirroring, and behavior features may be extracted from the packet data.

Here, at step S220, the packet data of the medical device may be collected from the port of a router into which the medical device plugs, through port mirroring.

Here, at step S220, behavior features may be extracted from the packet data collected in the process whereby access by the medical device to the network is initialized.

Here, at step S220, behavior features may be extracted from packet data collected depending on the re-operation of the medical device after access by the medical device to the network has been initialized.

Here, at step S220, the behavior features may be extracted from the average data traffic of the packet data, a protocol, a port, an operation cycle, and a communication pattern.

Next, the device identification method based on network behavior according to the embodiment of the present invention may analyze the behavior features and then generate unique information at step S230.

That is, at step S230, the behavior features may be analyzed based on the previously created detection model, and then a phenotype fingerprint which is unique information may be generated.

At step S230, the phenotype fingerprint, which is the unique information, may be generated through time-series packet analysis using a predefined deep-learning technique.

Next, the device identification method based on network behavior according to the embodiment of the present invention may identify the medical device at step S240.

That is, at step S240, an identification number corresponding to the unique information may be extracted from the medical device profile DB 10, and then the medical device may be identified.

In detail, at step S240, when the result of determining the similarity between the phenotype fingerprint stored in the medical device profile DB 10 and the phenotype fingerprint generated from the behavior features is equal to or greater than a preset threshold value, an identification number corresponding to the phenotype fingerprint stored in the medical device profile DB 10 may be extracted.

Here, at step S240, the extracted medical device identification number and the identification number of the router/switch, to which the medical device is connected, may be transmitted to the medical device security management server.

Here, at step S240, a medical device security management server may check the physical location at which the router is installed based on the router identification number, may ascertain the physical location of the detected medical device, may notify the network-behavior-based device identification apparatus 100 of information about the physical location and network access information (e.g., the IP address, the router to which the medical device is connected, etc.), and may store the physical location information and the network access information in a medical device management DB.

Here, at step S240, the medical device corresponding to the identification number may be identified from the medical device profile DB 10, and the pre-registered physical location of the medical device may be checked from the medical device security management server.

Here, at step S240, when the behavior features are changed, an identification number corresponding to the medical device profile DB 10 may be extracted from a phenotype fingerprint corresponding to the changed behavior features, and the change in the physical location of the medical device may be verified.

Here, at step S240, a security policy and a security level for the medical device may be established based on the identification number, and security management service corresponding to the security policy and the security level may be provided to the medical device.

Figure 9:
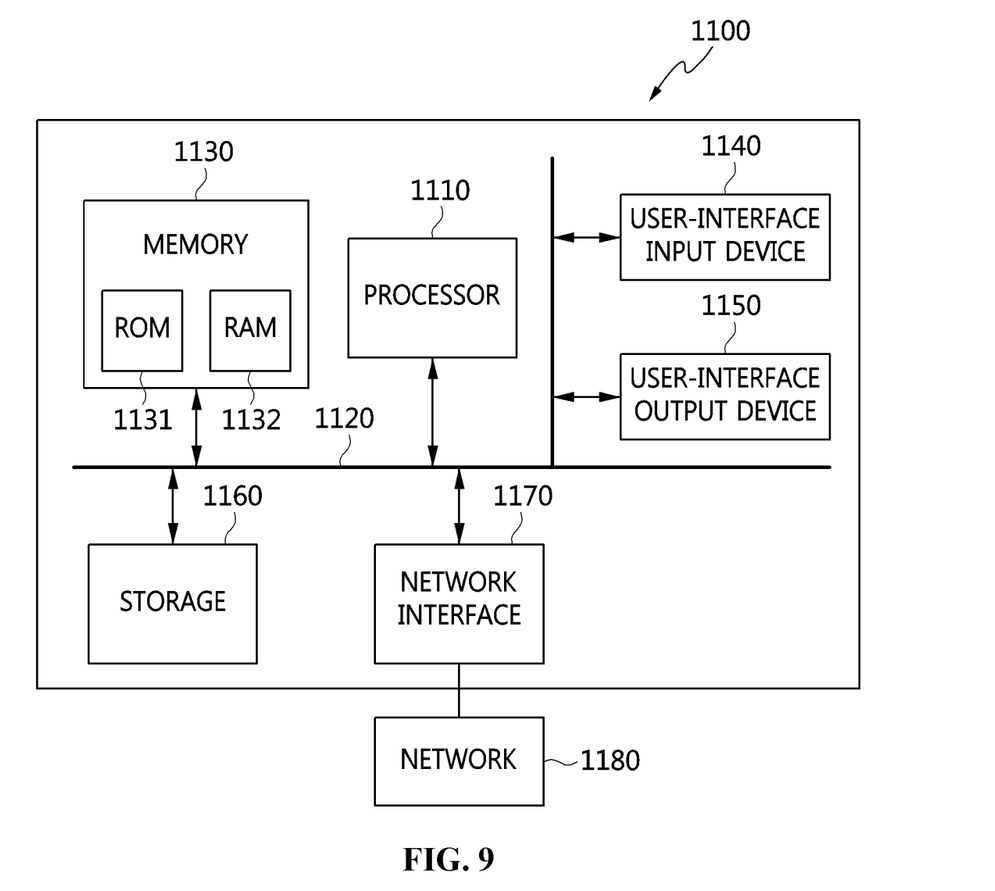
FIG. 9 is a block diagram illustrating a computer system according to an embodiment of the present invention.

FIG. 9 is a block diagram illustrating a computer system according to an embodiment of the present invention.

Referring to FIG. 9, a device identification apparatus based on network behavior according to an embodiment of the present invention may be implemented in a computer system 1100, such as a computer-readable storage medium. As illustrated in FIG. 9, the computer system 1100 may include one or more processors 1110, memory 1130, a user interface input device 1140, a user interface output device 1150, and storage 1160, which communicate with each other through a bus 1120. The computer system 1100 may further include a network interface 1170 connected to a network 1180. Each processor 1110 may be a Central Processing Unit (CPU) or a semiconductor device for executing processing instructions stored in the memory 1130 or the storage 1160. Each of the memory 1130 and the storage 1160 may be any of various types of volatile or nonvolatile storage media. For example, the memory 1130 may include Read-Only Memory (ROM) 1131 or Random Access Memory (RAM) 1132.

The device identification apparatus based on network behavior according to an embodiment of the present invention may include one or more processors 1110 and execution memory 1130 for storing at least one program executed by the one or more processors 1110, wherein the at least one program is configured to collect packet data of a device connected to a network through port mirroring and extract behavior features from the packet data, analyze the behavior features and then generate unique information based on a previously created detection model, and extract an identification number corresponding to the unique information from a database and then identify the device.

Here, the at least one program may be configured to collect the packet data of the device from a port of a router into which the device plugs, through the port mirroring.

Here, the at least one program may be configured to extract behavior features from the packet data collected in a process whereby access by the device to the network is initialized.

Here, the at least one program may be configured to extract behavior features from packet data collected depending on a re-operation of the device after access by the device to the network has been initialized.

Here, the at least one program may be configured to extract the behavior features from an average data volume of the packet data, a protocol, a port, an operation cycle, and a communication pattern.

Here, the at least one program may be configured to generate the unique information through time-series packet analysis using a predefined deep-learning technique.

Here, the at least one program may be configured to, when a result of determining a similarity between unique information stored in the database and the unique information generated from the behavior features is equal to or greater than a preset threshold, extract the identification number corresponding to the unique information stored in the database.

Here, the at least one program may be configured to identify the device corresponding to the identification number from the database and ascertain a pre-registered physical location of the device.

Here, the at least one program may be configured to, when the behavior features are changed, extract an identification number corresponding to the database from unique information of the changed behavior features and check a change in a physical location of the device.

Here, the at least one program may be configured to establish a security policy and a security level for the device from the identification number and provide a security management service corresponding to the security policy and the security level to the device.

The present invention may automatically identify a device when the corresponding device is operated in the state in which the device is connected to a network.

Further, the present invention may provide efficiency device management by identifying network access information for a device, the physical location of the device, etc.

Furthermore, the present invention may provide additional security functions, such as access control for a device and establishment of security policies for the corresponding network.

As described above, in the device identification apparatus and method based on network behavior according to the present invention, the configurations and schemes in the above-described embodiments are not limitedly applied, and some or all of the above embodiments can be selectively combined and configured such that various modifications are possible.

What is claimed is:

1. A device identification apparatus based on network behavior, comprising:
one or more processors; and
an execution memory for storing at least one program that is executed by the one or more processors,
wherein the at least one program is configured to:
collect packet data for a preset period of time of a device connected to a network through port mirroring and extract behavior features from the packet data, wherein the extraction of behavior features corresponds to an average amount of data that is transmitted during the preset period, a protocol used by the device, information about a network access port, an operation cycle including information about an idle/activation ratio and information indicating whether a distribution of operation of the device is periodic or aperiodic, and a communication pattern comprising information about a change in directionality, destination diversity, port diversity and data volume diversity, analyze the behavior features and then generate unique information based on a previously created detection model, and extract an identification number corresponding to the unique information from a database and then identify the device.

2. The device identification apparatus of claim 1, wherein the at least one program is configured to collect the packet data of the device from a port of a router into which the device plugs, through the port mirroring.

3. The device identification apparatus of claim 2, wherein the at least one program is configured to extract behavior features from the packet data collected in a process whereby access by the device to the network is initialized.

4. The device identification apparatus of claim 3, wherein the at least one program is configured to extract behavior features from packet data collected depending on a re-operation of the device after access by the device to the network has been initialized.

5. The device identification apparatus of claim 2, wherein the at least one program is configured to generate the unique information through time-series packet analysis using a predefined deep-learning technique.

6. The device identification apparatus of claim 5, wherein the at least one program is configured to, when a result of determining a similarity between unique information stored in the database and the unique information generated from the behavior features is equal to or greater than a preset threshold, extract the identification number corresponding to the unique information stored in the database.

7. The device identification apparatus of claim 6, wherein the at least one program is configured to identify the device corresponding to the identification number from the database and ascertain a pre-registered physical location of the device.

8. The device identification apparatus of claim 7, wherein the at least one program is configured to, when the behavior features are changed, extract an identification number corresponding to the device from the database and check a change in a physical location of the device.

9. The device identification apparatus of claim 8, wherein the at least one program is configured to establish a security policy and a security level for the device from the identification number and provide a security management service corresponding to the security policy and the security level to the device.

10. A device identification method based on network behavior, the device identification method being performed by a device identification apparatus based on network behavior, the device identification method comprising:

collecting packet data for a preset period of time of a device connected to a network through port mirroring and extract behavior features from the packet data, wherein the extraction of behavior features corresponds to an average amount of data that is transmitted during the preset period, a protocol used by the device, information about a network access port, an operation cycle including information about an idle/activation ratio and information indicating whether a distribution of operation of the device is periodic or aperiodic, and a communication pattern comprising information about a change in directionality, destination diversity, port diversity and data volume diversity;

analyzing the behavior features and then generating unique information based on a previously created detection model; and extracting an identification number corresponding to the unique information from a database and then identifying the device.

11. The device identification method of claim 10, wherein extracting the behavior features is configured to collect the packet data of the device from a port of a router into which the device plugs, through the port mirroring.

12. The device identification method of claim 11, wherein extracting the behavior features is configured to extract behavior features from the packet data collected in a process whereby access by the device to the network is initialized.

13. The device identification method of claim 12, wherein extracting the behavior features is configured to extract behavior features from packet data collected depending on a re-operation of the device after access by the device to the network has been initialized.

14. The device identification method of claim 11, wherein generating the unique information is configured to generate the unique information through time-series packet analysis using a predefined deep-learning technique.

15. The device identification method of claim 14, wherein identifying the device is configured to, when a result of determining a similarity between unique information stored in the database and the unique information generated from the behavior features is equal to or greater than a preset threshold, extract the identification number corresponding to the unique information stored in the database.

16. The device identification method of claim 15, wherein identifying the device is configured to identify the device corresponding to the identification number from the database and ascertain a pre-registered physical location of the device.

17. The device identification method of claim 16, wherein identifying the device is configured to, when the behavior features are changed, extract an identification number corresponding to the device from the database and check a change in a physical location of the device.

18. The device identification method of claim 17, wherein identifying the device is configured to establish a security policy and a security level for the device from the identification number and provide a security management service corresponding to the security policy and the security level to the device.

* * * * *